(12) United States Patent
Lee

(10) Patent No.: US 11,554,150 B2
(45) Date of Patent: Jan. 17, 2023

(54) PREPARATION METHOD OF A CANNABIS EXTRACT COMPOSITION FOR PAIN RELIEF, STRESS-RELATED DISEASE PREVENTION, OR STRESS RELATED DISEASE TREATMENT

(71) Applicant: FAMENITY CO., LTD., Uiwang-si (KR)

(72) Inventor: Ji Won Lee, Gwacheon-si (KR)

(73) Assignee: FAMENITY CO., LTD., Uiwang-si (KR)

( * ) Notice: Subject to any disclaimer, the term of this patent is extended or adjusted under 35 U.S.C. 154(b) by 0 days.

(21) Appl. No.: 17/516,581

(22) Filed: Nov. 1, 2021

(65) Prior Publication Data

US 2022/0047661 A1 Feb. 17, 2022

Related U.S. Application Data

(63) Continuation of application No. 16/778,098, filed on Jan. 31, 2020, now abandoned.

(51) Int. Cl.
*A61K 36/185* (2006.01)
*A61K 31/352* (2006.01)
*A23L 33/105* (2016.01)
*A61P 29/00* (2006.01)
*A61K 9/00* (2006.01)
*A61P 25/00* (2006.01)

(52) U.S. Cl.
CPC .......... *A61K 36/185* (2013.01); *A23L 33/105* (2016.08); *A61K 9/0014* (2013.01); *A61K 31/352* (2013.01); *A61P 25/00* (2018.01); *A61P 29/00* (2018.01)

(58) Field of Classification Search
None
See application file for complete search history.

(56) References Cited

FOREIGN PATENT DOCUMENTS

JP          2003146844 A    *  5/2003

* cited by examiner

*Primary Examiner* — Michael V Meller
(74) *Attorney, Agent, or Firm* — STIP Law Group, LLC

(57) ABSTRACT

The present invention relates to a method of preparation of a cannabis extract composition comprising a cannabis extract as an active ingredient for relieving pain and preventing or alleviating a stress-involved disease by suppressing a cyclooxygenase (COX)-2 enzyme and preventing dopamine and serotonin from being suppressed.

1 Claim, 2 Drawing Sheets

[FIG. 1]
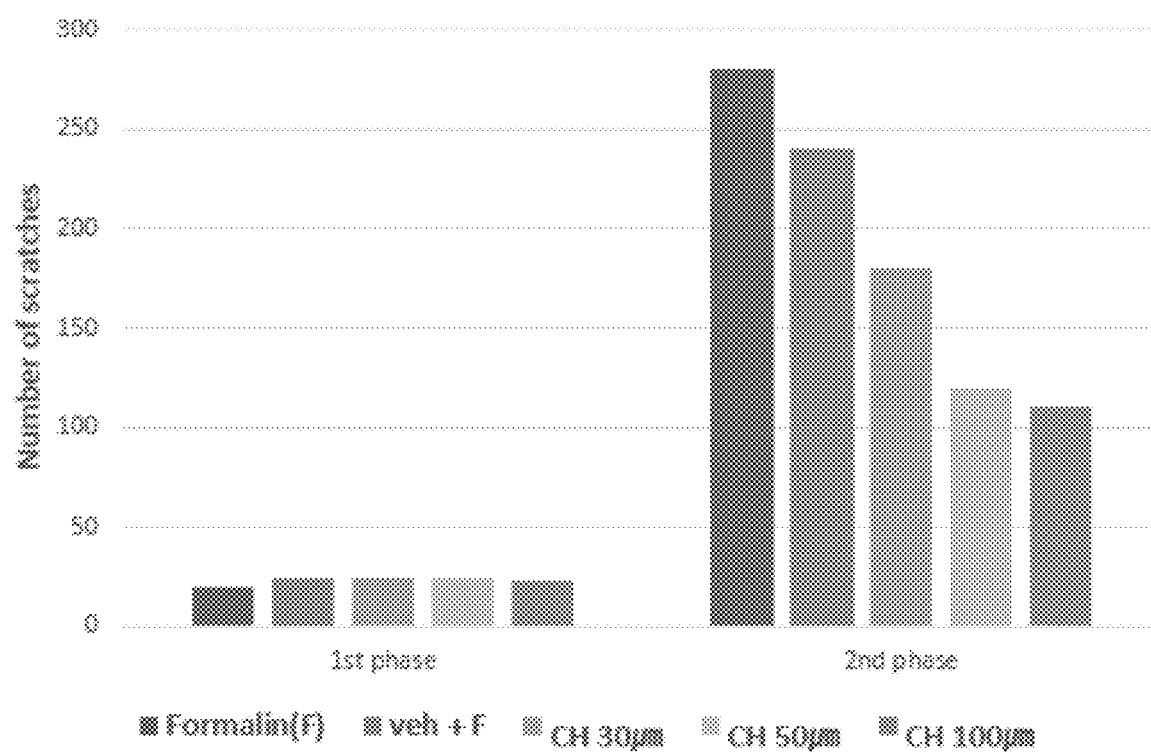

[FIG. 2]
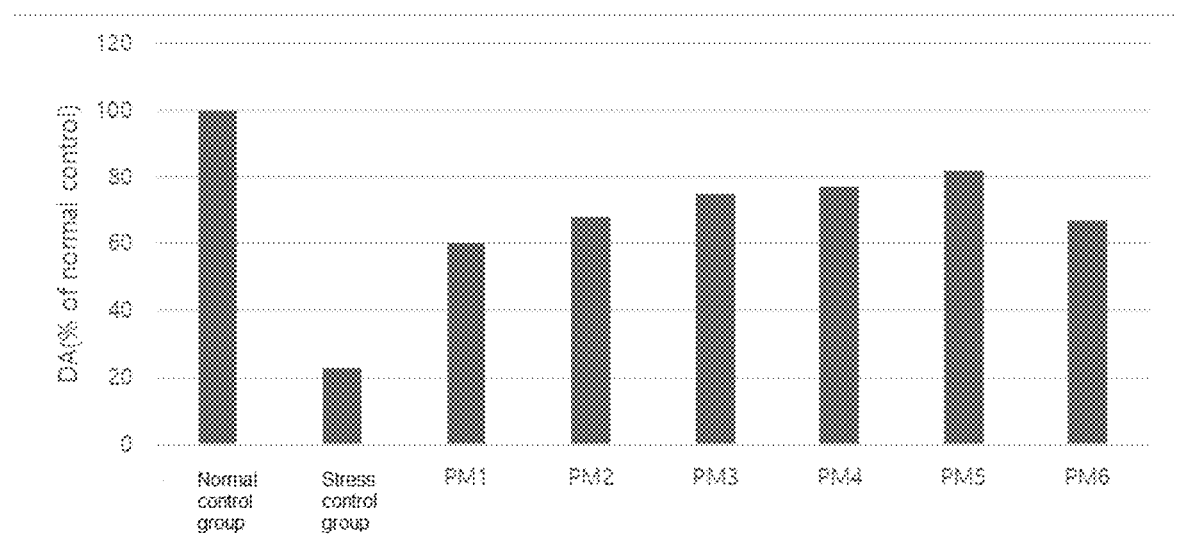
[FIG. 3]
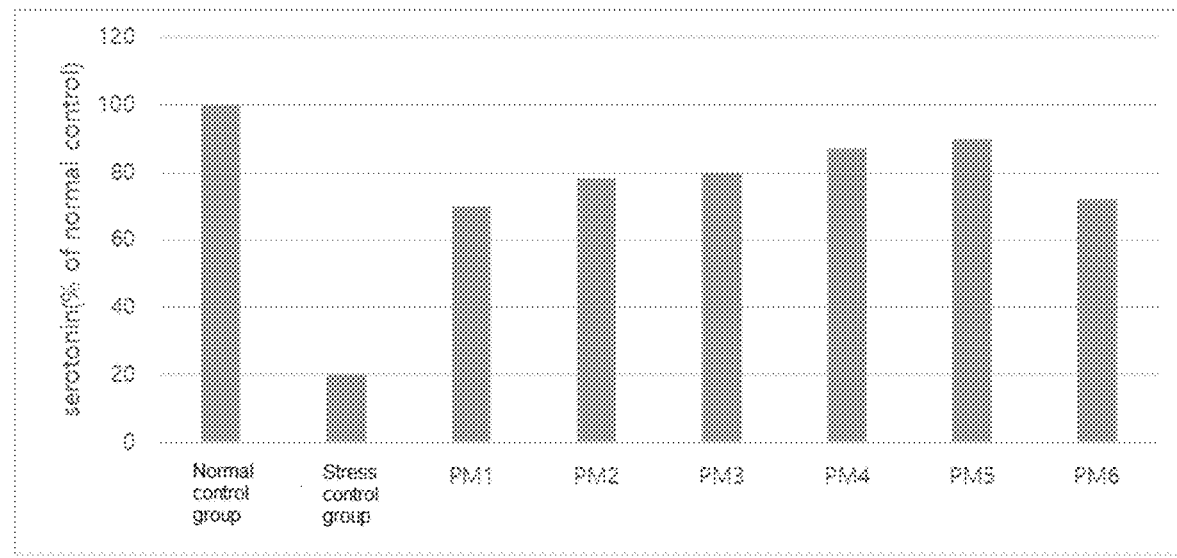

PREPARATION METHOD OF A CANNABIS EXTRACT COMPOSITION FOR PAIN RELIEF, STRESS-RELATED DISEASE PREVENTION, OR STRESS RELATED DISEASE TREATMENT

CROSS-REFERENCE TO RELATED APPLICATIONS

This application is a continuation of U.S. application Ser. No. 16/778,098 filed on Jan. 31, 2020, the disclosures of which are incorporated by reference into the present application.

TECHNICAL FIELD

The present invention relates to a method of preparation of a cannabis extract composition comprising a cannabis extract as an active ingredient for relieving pain and preventing or alleviating a stress-involved disease. More particularly, the present invention relates to a composition for relieving pain and preventing or alleviating a stress-involved disease, which suppresses a cyclooxygenase (COX)-2 enzyme and simultaneously prevents dopamine and serotonin from being suppressed by using a cannabis extract.

BACKGROUND ART

Today, as the society develops and diversifies rapidly, the society requires modern people to perform various roles. Accordingly, the number of people complaining of anxiety disorders and mental illness due to various types of stress is increasing. Recently, in consideration of the tendency of adolescents to increase mental illness due to excessive academic fever or various types of stress, this may be considered as a tendency of various types of stress and accompanying mental illness to be gradually increasing.

Here, when the mechanism of changes in neurotransmitters and hormones related to stress is briefly described, the hypothalamus in the body is responsible for secretion of neurotransmitters and hormones against external stimuli and stress, and the release of neurotransmitters such as dopamine, noradrenaline and serotonin from each nerve terminal is regulated by the signal from the hypothalamus to the central nervous system, so that the emotional state, heart rate, and physiological activities such as blood pressure and skeletal muscle blood flow are regulated.

Further, hormones are secreted into the blood through the hypothalamic-pituitary-adrenal (HPA) axis system, which is a hormonal circulatory system that is connected from the hypothalamus to the pituitary-adrenal gland. If a human is subjected to external stimuli or stress, the hypothalamus in the body secretes a corticotropin-releasing factor (CRF). Thereafter, when the secreted CRF binds to a receptor that specifically binds to a CRF in the pituitary, an adrenocorticotropic hormone (ACTH) is secreted.

When the secreted ACTH reaches the adrenal gland through the blood and lymph nodes, steroid hormones such as corticosterone from the cortex and catecholamine hormones from the pulp are released into the blood, and thus are involved in the regulation of heart rate, blood pressure, energy metabolism, and the like, and the secretion of these factors is regulated through negative feedback regulation.

Serotonin is a neurotransmitter found in the cerebrospinal fluid, and circulates through the brain and functions as a neurotransmitter. The serotonin is closely related to emotional expression, and deficient serotonin may cause emotional instability, which leads to an increase in worry and concern, and impulsive tendencies appear. Since the serotonin deficiency is closely related to depression, many drugs currently used to treat depression prevent serotonin from being reabsorbed and remain in the brain for a long time.

Meanwhile, depression as referred to in the present invention is defined not only as the dictionary meaning of depression, but also as a meaning including anxiety or anxiety disorder.

Anxiety is a mental illness that usually shows persistent and unrecovered hypersensitivity, tension, worry, and the like usually for six months or more, and extreme fear is felt for every trivial event beyond normal response without any special reason. The fear is generally caused by structural and functional abnormalities of the brain and continuous stress, and especially in the case of children and adolescents, when attention deficit hyperactivity disorder (ADHD), and the like are severe, the fear may be linked to anxiety and depression. Anxiety is broadly classified into four types such as generalized anxiety disorder, obsessive-compulsive disorder, panic disorder and post-traumatic stress disorder, and in particular, generalized anxiety disorder, which accounts for the largest proportion, is an overly widespread feeling of anxiety, and unsubstantiated free-floating anxiety and autonomic hypersensitivity appear as the largest features.

Currently, anxiety in the clinic is treated in combination with drug treatment and long-term psychiatric treatment. In the case of drug treatment, benzodiazepine-based anxiolytic drugs such as diazepam, lorazepam, clonazepam, and alprazolam are usually used, and an azapirone-based buspirone acts as a partial efficacy drug at the serotonin receptor and has been used as a drug capable of more selectively alleviating anxiety symptoms. Moreover, imidazopyridine-based drugs such as zolpidem have been used for treating short-term insomnia caused by anxiety.

However, the drugs used for treating anxiety disorders and mental illness are mostly drugs classified as psychotropic medicines, and in particular, benzodiazepine-based drugs act directly on the gamma-aminobutyric acid (GABA) receptor in the central nervous system to suppress the central nervous system, resulting in excessive sedative action, and in addition, the GABA suppressive action may be enhanced, and the central suppressive action such as depression, muscle relaxation, and hypnosis may be enhanced and appear. In addition, drugs used for treating anxiety disorders and mental illnesses make people psychologically and physically rely on the drugs, and thus involve risks such as concern about drug abuse.

Therefore, there is a need for the development of health functional foods and the like that have an effect on mental illness, do not cause excessive sedation and drowsiness, and can prevent non-dependent drugs or stress stimuli from developing into mental illness.

Furthermore, such stress stimuli may represent a headache with a tight, heavy, or tingling sensation in the head. Most people feel pain on both sides of the head, and mainly use pharmacotherapy for treatment, but a natural composition needs to be used, such that there is no problem of side effects caused by the dosage and the duration of taking medicine.

PRIOR ART DOCUMENT

Patent Document (Patent Document 1) KR 10-2010-0106062 A

SUMMARY OF THE INVENTION

The present invention has been made in an effort to provide a composition for relieving pain and preventing or alleviating a stress-involved disease, including a cannabis extract as an active ingredient.

The present invention has also been made in an effort to provide a composition for relieving pain and preventing or alleviating a stress-involved disease, which suppresses a cyclooxygenase (COX)-2 enzyme of a cannabis extract and simultaneously prevents dopamine and serotonin from being suppressed.

The present invention has also been made in an effort to provide a composition for relieving pain and preventing or alleviating a stress-involved disease, which has excellent effects of alleviating pain and preventing or alleviating the stress-involved disease, and has no side effects when taken or administered.

An exemplary embodiment of the present invention provides a composition for relieving pain and preventing or alleviating a stress-involved disease according to an exemplary embodiment of the present invention includes a cannabis extract as an active ingredient.

The cannabis extract includes cannabinoids and terpene.

The stress-involved disease is any one selected from the group consisting of stress, depression, and insomnia.

The composition exhibits an effect of relieving pain by suppressing a cyclooxygenase (COX)-2 enzyme.

The composition prevents or alleviates a stress-involved disease by preventing dopamine and serotonin from being suppressed.

The extract includes those extracted using an extraction solvent selected from the group consisting of water, $C_1$ to $C_6$ lower alcohols, and a mixture thereof.

A functional food according to another exemplary embodiment of the present invention is prepared using a composition for relieving pain and preventing or alleviating a stress-involved disease, including a cannabis extract as an active ingredient.

A skin external preparation according to still another exemplary embodiment of the present invention is prepared using a composition for relieving pain and preventing or alleviating a stress-involved disease, including a cannabis extract as an active ingredient.

A medicament according to yet another exemplary embodiment of the present invention is prepared using a composition for relieving pain and preventing or alleviating a stress-involved disease, including a cannabis extract as an active ingredient.

Hereinafter, the present invention will be described in more detail.

As used herein, the term 'extract' has a meaning commonly used as a crude extract in the art as described above, but also includes a fraction obtained by additionally fractionating an extract in a broad sense. That is, an extract includes not only those obtained using the above-described extraction solvent, but also those obtained by additionally applying a purification process. For example, a fraction obtained by allowing the extract to pass through an ultra-filtration membrane having a predetermined molecular weight cut-off value, and a fraction obtained through various purification methods such as separation by means of various chromatography methods (those manufactured for separation according to the size, charge, and hydrophobicity or hydrophilicity) additionally carried out are included in the extract of the present invention.

To achieve the objects, a composition for relieving pain and preventing or alleviating a stress-involved disease according to an exemplary embodiment of the present invention includes a cannabis extract as an active ingredient.

Cannabis is an annual plant of the Cannabaceae family, and the subspecies thereof are classified into three subspecies such as *C. sativa* subsp. *sativa, C. sativa* subsp. *indica,* and *C. sativa* subsp. *ruderalis.* It is known that cannabis has been widely cultivated for about 12,000 years, mainly in Central Asia, in tropical and temperate regions, when legal regulations had not been applied in the past, and cannabis was used for food in China around 6,000 BC. There is a record of using fiber obtained from cannabis around 4,000 BC, and there is a document in the Chinese herbal book that cannabis was first used for medical purposes in 2,727 BC. However, in the twentieth century, cannabis has been strictly regulated in cultivation and handling not only in Korea but also in most countries due to side effects such as hallucinations. However, the importance of cannabis for its excellent pharmacological action has been increasingly recognized overseas, and there is an increasing movement to permit the use of cannabis for therapeutic purposes. In Korea, studies on cannabis are lacking due to strict regulations on cannabis, and in particular, there have been almost no studies on efficacy verification for medical cannabis and problems on toxicity.

In the past, cannabis was used in various manners depending on the site, and hemp or cannabis leaves as hemp leaves are said to have an action of killing roundworms, and washing hair with water boiled with cannabis leaves is said to causes hair to grow long and shine. Further, cannabis has been used for asthma or prolonged coughing, roundworm, analgesic action, anesthetic, and diuretic. The root of cannabis refers to magen, and was believed to treat difficult delivery and the absence of the placenta, relieve static blood, and alleviate stone strangury, and it was said that as a method of taking the root of cannabis, the root of cannabis was decocted and the decocted water was taken. Mapi as the skin of cannabis was said to treat bruise and heat strangury pain, and mahua as the flower of cannabis was said to be used for treating paralysis and itching. The flower spike of cannabis refers to mafen, and has been utilized for difficult delivery, constipation, gout, madness, insomnia, and the like. The cannabis extract includes cannabinoids and terpene.

To date, about 400 compounds have been found in cannabis, most of which are cannabinoids, terpenes, and phenolic compounds. Among them, cannabinoids have been known as a representative active ingredient of cannabis, but to date, about 90 kinds of cannabinoids have been revealed, and many ingredients found only in cannabis are also known. Cannabinol (CBN) was separated from cannabis in 1899, but later it was known that cannabinol (CBN) was not a single compound, and after cannabidiol (CBD) and tetrahydrocannabinol (THC), which are pure compounds purified from cannabis, were isolated in the 1930s, studies on ingredients of cannabis became more active.

Efforts to develop drugs using specific ingredients of cannabis have continued, and among them, THC and CBD, the main compounds of medical cannabis have received the most attention for therapeutic purposes. Studies have shown that CBD has no psychotropic effects and is effective in reducing pain and modulating epileptic seizures.

In addition, 100 or more terpene-based compounds that serve to produce the aroma and taste of cannabis have been identified in cannabis, and are present in the form of various monoterpenoids and sesquiterpenoids. Although terpene has been shown to be associated with various pharmacological effects such as anti-inflammatory effects, studies on terpene compounds extracted from cannabis have been insufficient compared to THC to date.

Furthermore, terpene is known to exhibit a better effect when acting with cannabinoids such as CBD and THC, and may improve absorption of cannabinoids, overcome bacterial defense mechanisms and minimize side effects.

The stress-involved disease is any one selected from the group consisting of stress, depression, and insomnia.

Stress refers to anxiety and threat emotions that a human perceives when he or she is placed in a psychologically or physically intolerable situation, and indicates a psychological response such as anxiety, depression, and frustration or a physical response such as loss of appetite.

Depression is an illness in which the function of the brain that regulates emotions is altered and 'negative emotions' appear, and is a disorder that affects 100 million or more people worldwide. The nature of depression is a physiological and anatomical problem, and the negative emotions correspond to the result caused by such changes in human body structure. A temporary feeling of depression is called 'depressive mood'. Causes of depressive mood include interpersonal relationship stress, financial problems, and the like.

Insomnia (sleep disorder) refers to a sleep induction disorder that has difficulty in sleeping and a sleep maintenance disorder in which one takes sleep but wakes up frequently or wakes up too early during sleep. If you do not sleep well at night, you will be in a sleep-deprived state, leading to daytime drowsiness, fatigue, loss of motivation, and the like, hindering your daily life and making the quality of life deteriorate. Insomnia usually occurs in people whose sleeping hours and habits are irregular, and the symptoms are aggravated while people are experiencing environmental changes and psychological stress. Even when you are too worried about insomnia itself, your nervous system may become nervous, causing insomnia to persist and become severe, and there are various causes of insomnia, but the common cause of temporary insomnia is a change in the regular rhythm of life caused by jet lag due to journey, new workplaces (jobs), relocations, hospitalizations, and the like.

When the stress-involved disease is chronic, symptoms such as pain, arthritis, headache, and dyspnea may be accompanied by insomnia.

Therefore, the present invention may show a pain relieving effect, and simultaneously prevent or alleviate the stress-involved disease as described above, using a cannabis extract.

The composition prevents or alleviates a stress-involved disease by preventing dopamine and serotonin from being suppressed.

Dopamine is one of the neurotransmitters and a precursor of a norepinephrine and epinephrine complex. Dopamine is one of the amino acids present in animals and plants, and plays a role in the transmission of excitation of brain nerve cells. Dopamine acts as a neurotransmitter in our brain. Dopamine neurons that secrete dopamine are located in the ventral tegmental area of the midbrain, the substantia nigra, the arcuate nucleus of hypothalamus, and the like. In the ventral tegmental area, dopaminergic innervation occurs in the cerebral cortex, the limbic system, and the like, and these are called the mesocortical pathway and the mesolimbic pathway, respectively. In the substantia nigra, dopaminergic innervation occurs in the striatum, and this is called the nigrostriatal pathway. Dopamine neurons (TIDA neurons) located in the arcuate nucleus of the hypothalamus perform dopaminergic innervation at the median eminence site through the tuberoinfundibular pathway.

The degree to which cells are excited or suppressed can be adjusted in a manner that dopamine molecules bind to dopamine receptors in neurons, and the dopamine receptors bind to a G protein (GTP-binding-protein) to activate second messengers or activate or suppress a specific signaling system.

Further, serotonin is one of the chemical substances that function as a neurotransmitter located at the center of the hypothalamus in the brain, and is closely related to emotional expression. Deficient serotonin may cause emotional instability, which leads to an increase in worry and concern, and make impulsive tendencies appear, and serotonin is a molecule that makes you feel happy, and is also called a happiness hormone even though serotonin is not a hormone. In addition to controlling mood, serotonin is involved in many functions related to appetite, sleep, and muscle contraction. Furthermore, serotonin is also related to thought function, affects memory and learning, is stored in platelets, and is involved in hemostasis and blood coagulation response. Serotonin is synthesized from L-tryptophan via a short pathway, and tryptophan hydroxylase and amino acid decaboxylase are involved in this reaction.

Lack of such serotonin results in depression, anxiety and the like. Further, serotonin acts as an important regulator in appetite and food choice and is known to be most related to carbohydrate intake. Appetite decreases when serotonin increases locally, and the opposite phenomenon occurs when serotonin decreases.

Therefore, a composition for relieving pain and preventing or alleviating a stress-involved disease of the present invention includes a cannabis extract as an active ingredient, and may exhibit effects of preventing or alleviating a stress-involved disease by preventing dopamine and serotonin from being suppressed.

The composition exhibits an effect of relieving pain by suppressing a cyclooxygenase (COX)-2 enzyme.

Cyclooxygenase (COX)-2 is an enzyme that induces the synthesis of the pain-inducing substance prostaglandin (PG), and since the synthesis is promoted by other stimuli including NO, suppression of the expression or activity of COX-2 also becomes an important marker for the treatment of pain.

The inflammatory response is induced by noxious stimuli or infections and begins with the production of prostaglandins (PG), leukotrienes (LT), and the like depending on the types of cells and stimuli, and is performed by cyclooxygenase-1 (COX-1) and cyclooxygenase-2 (COX-2). COX-1 and COX-2 are isomeric forms with almost the same identity, COX-1 is present in most cells and acts on gastric mucosal protection, platelet coagulation, and normal biological function involved in blood flow in the kidneys, whereas COX-2 is induced and expressed in a short time by inflammatory stimuli, and is an enzyme present in macrophages, mononuclear cells, and the like, which are amplified under inflammatory conditions, and is known to be closely related to inflammation, pain, fever, anemia, and the like.

Therefore, the composition for relieving pain and preventing or alleviating a stress-involved disease of the present invention includes a cannabis extract as an active ingredient, and may exhibit an effect of relieving pain by suppressing a cyclooxygenase (COX)-2 enzyme.

Preferably, the composition for relieving pain and preventing or alleviating a stress-involved disease may further include an *Erigeron annuus* (L.) *Pers* extract, a *Ceratonia siliqua* (L.) *Taub*. extract, and a *Stellaria media* extract.

The *Erigeron annuus* (L.) *Pers* is a native of North America, a biennial grass growing in fields, plains and roadsides in various parts of Korea, and a genus *Chrysanthemum* plant, and various physiological activities thereof such as dyspepsia, malaria, enteritis, hepatitis, diuretic action or hypoglycemic action are known.

The *Ceratonia siliqua* (L.) *Taub.* is s an evergreen broad-leaved shrub that grows about 10 m in height, and is well tolerated by drought. The leaves contain resin. In the fall, small faint green-brown flowers bloom and long green pods run. The pods, when ripe, turn chocolate-colored and contain small, glossy, and hard beans therein. Carob gum, which softens the skin, is popular as a skin pack and is also used to treat diarrhea.

The *Stellaria media* is a biennial herb of the family Caryophyllaceae, grows mainly on a roadside or in an embankment around the end of a field, is about 10 to 20 cm tall, and is rich in minerals such as protein, calcium and iron. The *Stellaria media* strengthens the stomach and intestines, cleanses the blood and improves milk production. The *Stellaria media* may also treat inflammation such as gum disease, tooth decay, appendicitis, enteritis, and bowel ulcers.

When the natural extracts are used in combination, the effects of relieving pain and preventing or alleviating a stress-involved disease are enhanced due to the mixing action among the constituent ingredients.

Further, as the *Erigeron annuus* (L.) *Pers* extract, the *Ceratonia siliqua* (L.) *Taub.* extract and the *Stellaria media* extract are additionally included, it is possible to provide a composition having excellent preference by neutralizing the taste and aroma peculiar to the cannabis extract.

Preferably, the composition of the present invention may include 20 to 40 parts by weight of the *Erigeron annuus* (L.) *Pers* extract, 20 to 40 parts by weight of the *Ceratonia siliqua* (L.) *Taub.* extract, and 20 to 40 parts by weight of the *Stellaria media* extract based on 100 parts by weight of the cannabis extract. When the composition of the present invention is used as a complex extract within the above-range, it is possible to exhibit the excellent effects of relieving pain and preventing or alleviating a stress-involved disease and simultaneously provide the composition as a composition having excellent preference.

The extract includes those extracted using an extraction solvent selected from the group consisting of water, $C_1$ to $C_6$ lower alcohols, and a mixture thereof.

Specifically, in order to prepare a cannabis extract, a natural extract may be obtained by including: grinding a natural product; leaching the ground product by using an organic solvent; leaching a sample, and then drying the sample; re-leaching the dried sample by using an organic solvent; leaching the sample, and then drying the sample; leaching the sample by using water; and leaching the resulting product.

The method of obtaining the natural extract may further include performing fractionation on the natural extract extracted by using the organic solvent by using an organic solvent.

The extraction solvent may be used 2 to 50 times, more specifically 2 to 20 times, based on the weight of the sample. For extraction, the sample may be left to stand in the extraction solvent for leaching for 1 to 72 hours, more specifically, 24 to 48 hours.

The extract may be prepared in a powder state by additional processes such as distillation under reduced pressure and freeze drying or spray drying, and the method include obtaining an extract by an extraction method selected from the group consisting of a solvent extraction method, an ultrasonic extraction method, a reflux extraction method, a leaching method, a fermentation method and a processing method.

The ultrasonic extraction method performs the reaction at 30 to 50° C. for 0.5 to 2.5 hours, and the extraction solvent is obtained from water or a 50 to 100% alcohol having 1 to 6 carbon atoms. Specifically, the extract is extracted at 40 to 50° C. for 1 to 2.5 hours, and an extraction solvent is obtained from water or a 70 to 80% alcohol having 1 to 6 carbon atoms.

The reflux extraction method is performed by 10 to 30 g of a ground material of the natural product based on water and 100 mL of an alcohol having 1 to 6 carbon atoms, a reflux time of 1 to 3 hours, and a 50 to 100% alcohol having 1 to 6 carbon atoms or water. More specifically, the method is performed by 10 to 20 g of a ground material of the natural product based on 100 mL of an alcohol having 1 to 6 carbon atoms or 100 mL of water, 10 to 20 g of a ground material of a natural product, a reflux time of 1 to 2 hours, and a 70 to 90% alcohol having 1 to 4 carbon atoms, or water.

The leaching method is performed at 15 to 30° C. for 24 to 72 hours, and as an extraction solvent, water or a 50 to 100% alcohol having 1 to 6 carbon atoms is used. More specifically, the leaching method is performed at 20 to 25° C. for 30 to 54 hours, and the extraction solvent is obtained by water or a 70 to 80% alcohol having 1 to 6 carbon atoms.

After extraction, the extract may be fractionated by sequentially applying new fractionation solvents. The fractionation solvent used during the fractionation is one or more selected from the group consisting of water, hexane, butanol, ethyl acetic acid, ethyl acetate, methylene chloride, and a mixture thereof, preferably, ethyl acetate or methylene chloride.

A functional food according to another exemplary embodiment of the present invention is prepared using a composition for relieving pain and preventing or alleviating a stress-involved disease, including a cannabis extract as an active ingredient.

"Functional food" as defined herein means a food manufactured and processed using raw materials or ingredients that have functional properties that are useful for the human body according to Act No. 6727 on functional foods, and "functional" is meant to be taken for the purpose of regulating nutrients to the structure and function of the human body, or obtaining effects useful for public health use, such as physiological effects.

A skin external preparation according to still another exemplary embodiment of the present invention is prepared using a composition for relieving pain and preventing or alleviating a stress-involved disease, including a cannabis extract as an active ingredient.

A medicament according to yet another exemplary embodiment of the present invention is prepared using a composition for relieving pain and preventing or alleviating a stress-involved disease, including a cannabis extract as an active ingredient. A dosage form of the medicament of the present invention may be in a preferred form according to the use method, and in particular, the medicament of the present invention may be formulated using a method publicly known in the art so as to provide a rapid, sustained, or delayed release of an active ingredient after being administered to mammals. Specific examples of the dosage form include granules, powders, syrups, solutions, suspensions, pills, infuses, tablets, suppositories, injections, spirits, capsules, pills, soft or hard gelatin capsules, and the like.

The preferred dose for the medicament of the present invention depends on the condition and body weight, the degree of the disease, the form of drug, the administration route and the duration, but may be appropriately selected by a person having ordinary skill in the art to which the present invention pertains.

By the composition for relieving pain and preventing or alleviating a stress-involved disease, including the cannabis extract of the present invention as an active ingredient, it is possible to provide a composition for relieving pain and preventing or alleviating a stress-involved disease, which suppresses a cyclooxygenase (COX)-2 enzyme and simultaneously prevents dopamine and serotonin from being suppressed by using a cannabis extract.

BRIEF DESCRIPTION OF THE DRAWINGS

FIG. 1 illustrates experimental results for the pain relief of a composition according to an exemplary embodiment of the present invention.

FIG. 2 illustrates the results of an experiment for measuring dopamine of a composition according to an exemplary embodiment of the present invention.

FIG. 3 illustrates the results of an experiment for measuring serotonin of a composition according to an exemplary embodiment of the present invention.

DETAILED DESCRIPTION

Hereinafter, the Examples of the present invention will be described in detail such that a person skilled in the art to which the present invention pertains can easily carry out the present invention. However, the present invention can be implemented in various different forms, and is not limited to the Examples described herein.

Preparation Example: Preparation of Extract

Preparation of Cannabis Extract

Cannabis including leaves and flowers was washed thoroughly with running water and then air-dried completely. The dried cannabis was pulverized with a mixer and then prepared as a powder. After 50% ethanol as an extraction solvent was added to the powder sample at a ratio of 1:10 (w:v) and then the powder sample was completely immersed, extraction was performed repeatedly three times at 80° C. under reflux for each 3 hours. The liquid extract was filtered with a Whatman No. 2 filter paper. A cannabis extract (CE) was prepared by concentrating the filtrate at 60° C. under reduced pressure.

2. Preparation of Other Natural Extracts

An *Erigeron annuus* (L.) Pers extract (EE), a *Ceratonia siliqua* (L.) Taub. extract (IE), and a *Stellaria media* extract (SE) were prepared using a method which is the same as the preparation method of the cannabis extract (CE).

3. Preparation of Complex Extract

A complex extract was formed by mixing the cannabis extract (CE), the *Erigeron annuus* (L.) Pers extract (EE), the *Ceratonia siliqua* (L.) Taub. extract (IE), and the *Stellaria media* extract (SE) as shown in the following Table 1.

TABLE 1

|    | MX1 | MX2 | MX3 | MX4 | MX5 | MX6 |
|----|-----|-----|-----|-----|-----|-----|
| CE | 100 | 100 | 100 | 100 | 100 | 100 |
| EE | —   | 10  | 20  | 30  | 40  | 50  |
| IE | —   | 10  | 20  | 30  | 40  | 50  |
| SE | —   | 10  | 50  | 30  | 40  | 50  |

(Unit: parts by weight)

Experimental Example 1: Cytotoxicity Experiments

In order to test the toxicity of cannabis extract (CE) and complex extracts (MX2 to MX6), differences in toxicity and side effects during the administration of the complex extracts were confirmed in a rat repetitive dose toxicity experiment.

Six-week-old SD male and female rats were divided into 10 per group (5 males and 5 females), and the complex extracts MX1 to MX6 were administered to the groups, and after each drug was dissolved in a 0.5% MC solution, oral administration once daily at the same morning time was repeated for 13 weeks.

As a single dose, the solution was administered in an amount of 3.75 mg/kg to 5 mg/kg. Thereafter, the mortality rate, general symptoms, weight change, and food and water intake were observed.

As a result, no dead individuals occurred during the experimental period. In view of the experimental results, it was confirmed that the cannabis extract (CE), the *Erigeron annuus* (L.) Pers extract (EE), the *Ceratonia siliqua* (L.) Taub. extract (IE), the *Stellaria media* extract (SE), and a mixture thereof had no toxicity problems.

Experimental Example 2: Effect of Relieving Pain

Cyclooxygenase (COX)-2 Inhibition Ability

The cannabis extract (CE), which was a sample used for the cyclooxygenase (COX)-2 enzyme inhibition ability measurement experiment, was dissolved in a DMSO solution and used. First, after the COX-2 enzyme, heme, and an inhibitory sample were put into a test tube containing a buffer for a reaction (the control group contained the same amount of DMSO instead of the inhibitory sample), the mixture was allowed to react at 37° C. for 10 minutes. After the reaction was completed for 10 minutes, 10 μL of a substrate (arachidonic acid) was added thereto, and the reaction was further performed for 2 minutes. When the reaction was completed, the reaction was terminated by adding 50 μL of a 1 M HCl solution thereto, and a reduction reaction was caused by adding tartaric acid. After each test tube reaction solution was diluted by 2000 fold and 4000 fold, 50 μL of the reaction solution was each added to a 96-well plate (well plate). After 50 μL of each of a tracer and antiserum was added thereto, the resulting mixture was allowed to react at 25° C. for 18 hours. After the reaction was terminated, the well was emptied and washed 5 times using a washing buffer, and then a coloring reagent was added thereto and the resulting mixture was allowed to react for 1 hour and 30 minutes. When the reaction was completed, the absorbance was measured at 405 nm using an ELISA reader.

As a result, the inhibition ability of the cannabis extract (CE) against COX-2 was the same as in Table 2. When each sample contained the same level (1 mg/mL) of the cannabis extract (CE), the sample exhibited 35.75% COX-2 enzyme inhibitory activity, whereas MX2 to MX6 exhibited an inhibitory activity of 58.57%, 60.38%, 62.47%, 61.97% and 60.27%, respectively. The complex extracts (MX2 to MX6) exhibited inhibitory activity by about 1.7 fold or more compared to MX1 which is a cannabis extract.

Therefore, as a result of inhibiting COX-2 enzyme, which is a synthase of prostaglandin (PG), it was confirmed that the complex extracts (MX2 to MX6) had better inhibitory effects than the cannabis extract at the same concentration.

TABLE 2

| | COX-2 inhibition ability |
|---|---|
| MX1 | 35.75 ± 2.45[1] |
| MX2 | 58.57 ± 8.08[2] |
| MX3 | 60.38 ± 5.41[2] |
| MX4 | 62.47 ± 2.41[2] |
| MX5 | 61.97 ± 9.06[2] |
| MX6 | 60.27 ± 4.41[2] |

(Unit: %)

Further, as a result of confirming the result in the complex extracts MX3 to MX5 showing the highest inhibitory effect, it was confirmed that the cyclooxygenase (COX)-2 inhibitory effect was excellent within the above-described range.

Formalin Pain Model Experiment of Cannabis Extract (CE)

An experiment for the effect of a cannabis extract (CE) on the relief of acute temporomandibular joint pain was performed using a temporomandibular joint (TMJ) pain model (Won, K. A., Kang, Y. M., Lee, M. K., Park, M. K., Ju, J. S., Bae, Y. C., et al. Participation of microglial p38 MAPK in formalin-induced temporomandibular joint nociception in rats. J Orofac Pain 2012; 26(2): 132-141.).

When the specific experimental method is described, experimental animals were acclimatized at 10 or more minutes in an experimental plastic bucket prior to pain response evaluation. 30 μl of 5% formalin was injected using an insulin syringe (0.25×8 mm), and it was observed that consciousness was restored within several seconds after the injection of formalin.

The position of the joint cavity was inferred from the lower inferior boundary surface of the zygomatic arch and mandibular condyle site using a digital exploration, and the site where the injection needle penetrated the joint capsule and touched the lower jaw was recognized to be in the joint cavity. Through a preliminary experiment, the position of the temporomandibular joint space was confirmed by injecting the same amount of a 1 w % evans blue dye as formalin into a separate animal. After the injection of formalin, rubbing or scratching the TMJ site and the face was considered a pain scale, a cumulative recording was performed consecutively 9 times for 45 minutes at an interval of 5 minutes, and an evaluation was performed by dividing the recorded results into a primary pain behavior response (0 to 10 minutes) and a secondary pain behavior response (11 to 45 minutes).

As a result, in an experiment using an animal (Rat), it could be seen that in a formalin-induced acute pain model administered to the temporomandibular joint, a change in pain behavior response upon administration of a cannabis extract (CE) appeared. For the primary pain behavior response, the cannabis extract-administered pain behavior response did not have a significant difference among a formalin injection group, a control group (veh+formalin injection group), and a cannabis extract (CE) injection group (30 μm, 50 μm, and 100 μm), but was effective for adjusting pain at the elapsed time point of 20 to 35 minutes corresponding to the second pain behavior response. These results are illustrated in FIG. 1, and through the result, it could be seen that the cannabis extract (CE) had a pain relieving effect.

Formalin Pain Model Experiment of Complex Extract

In order to investigate the effect of the complex extracts (MX2 to MX6) on the pain relief, the same experiment as the experiment of the cannabis extract (CE) was performed, and the results thereof are shown in comparison with the relative effect on cannabis extract (CE).

For the pain relief effect compared to the cannabis extract (CE), the CE was set at an index of 5, and the temporomandibular joint pain relief of MX2 to MX6 was evaluated as an index of 1 to 10. It can be said to mean that the higher the index is, the better the pain relief effects are.

TABLE 3

| | CE | MX2 | MX3 | MX4 | MX5 | MX6 |
|---|---|---|---|---|---|---|
| Temporomandibular joint pain model | 5 | 6 | 7 | 8 | 7 | 6 |

(Unit: Index)

As shown in Table 3 above, it was confirmed that the complex extracts MX2 to MX6 relieved pain equivalent to or greater than the cannabis extract (CE). This can be said to mean that when the natural complex extract is used, the effect in which pain is reduced is excellent due to the complex action of each ingredient, compared to when only the cannabis extract (CE) is used.

Experimental Example 3: Effects of Preventing and Improving Stress 4-week-old ICR male mice {SAMTAKO Bio Korea, Korea} were subjected to an adaptation time of 1 week, and then bred in a space where lighting is turned on and off repeatedly in a unit of 12 hours, and an indoor temperature of 18 to 23° C. and a humidity of 60% were maintained. As a feed, a solid feed was supplied, and there was no restriction on the feed or grade other than the process of inducing stress.

After the complex extracts (MX1 to MX6) in the Preparation Example were dissolved in distilled water, the resulting solutions were orally administered (40 mg/kg) continuously once a day at 14:00 to 15:00 for one month. The experimental group consisted of a total of three groups, which are a control group to which only stress was applied, a group to which the complex extracts (MX1 to MX6) were administered, and a normal control group to which neither stress nor extract was given. Five experimental animals were used for each experimental group, and stress was induced every day for 4 weeks from day 7 day after administration.

The stress-inducing method is used by modifying the method of Wilner et al. (Reduction of sucrose preference by chronic unpredictable mild stress, 1987), and specifically, stress is induced by creating a variety of unexpected mentally stressful situations such as fasting, dietary restriction after fasting (feeding a small amount of feed), suspension of water supply, provision of empty jugs after suspension of water supply, tilted breeding farm, breeding of a number of experimental animals in a breeding farm, sparkling light, cold room, and continuous light.

After the test animal in which the stress was induced was sacrificed by dislocation of the cervical vertebra, the brain was removed and the hippocampus tissue was put into a cooling tube and rapidly cooled. Each tissue sample was treated with 0.4 M perchloric acid and sonicated, and then centrifuged under a condition of 12,000 rpm (4° C.) using a centrifuge, and used for analysis. The analysis was carried out using a high performance liquid chromatography with electrochemical detection (HPLC-ECD) method with a slight modification of the method such as Qi.

Effect of Preventing Suppression of Dopamine

Dopamine is a precursor of norepinephrine as a neurotransmitter in the central nervous system, and is involved in cognition and attention concentration, reward, regulation of motor function, and the like. Since it is known that dopamine secretion is inhibited in a chronic stress situation, the stress prevention and improvement effects caused by the composition of the present invention were confirmed through a dopamine measurement experiment.

As a result of measuring the dopamine concentration using the high performance liquid chromatography with electrochemical detection (HPLC-ECD) method, the value (% of control) compared with the dopamine concentration of the normal control group was shown as an average and standard error. The administration group of the cannabis extract (CE, MX1), the administration groups of the complex extracts (MX2 to MX6), and the stress control group were compared by verifying the significance with a statistical treatment using a Student's T-test, and p<0.05 was considered to be significant and displayed. The results are illustrated in FIG. 2.

Referring to FIG. 2, it can be seen that the concentration of dopamine measured from the hippocampus of the test animals subjected to stress is remarkably lower than that in the normal control group. However, it can be seen that in the groups to which the cannabis extract (CE) and the complex extracts (MX2 to MX6) were administered, the concentration of dopamine was maintained higher than that in the stress control group.

In particular, it can be said to mean that when the natural complex extracts MX3 to MX5 are used, the effect of suppressing the reduction of dopamine is excellent due to the complex action of each ingredient, compared to when only the cannabis extract (CE, MX1) is used.

Therefore, in the case of the above range, it can be seen that the effect of preventing or alleviating stress is shown by suppressing the reduction of dopamine caused by stress.

Effect of Preventing Suppression of Serotonin

As a result, the value (% of control) compared with the serotonin concentration of the normal control group was expressed as the mean and standard error. The administration group of the cannabis extract (CE, MX1), the administration groups of the complex extracts (MX2 to MX6), and the stress control group were compared by verifying the significance with a statistical treatment using a Student's T-test, and p<0.05 was considered to be significant and displayed. The results are illustrated in FIG. 3.

Referring to FIG. 3, it can be seen that the concentration of serotonin measured from the hippocampus of the test animals subjected to stress is remarkably lower than that in the normal control group. However, it can be seen that in the groups to which the cannabis extract (CE) and the complex extracts (MX2 to MX6) were administered, the concentration of serotonin was maintained higher than that in the stress control group.

In particular, it can be said to mean that when the natural complex extracts MX3 to MX5 are used, the effect of suppressing the reduction of serotonin is excellent due to the complex action of each ingredient, compared to when only the cannabis extract (CE, MX1) is used.

Therefore, in the case of the above range, it can be seen that the effect of preventing or alleviating stress is shown by suppressing the reduction of serotonin caused by stress.

Experimental Example 4: Preference Test

Sensory Evaluation Test

Tea beverages were prepared by diluting MX1 and the complex extracts MX3 to MX6. The tea beverages were sampled by 10 tasters, and the taste and aroma were expressed by an index of 1 to 10, and the average values (applied to a rounding of 0.5) are shown in the following Table 4. The higher the number of the index is, the higher the preference is.

TABLE 4

|  | MX1 | MX2 | MX3 | MX4 | MX5 | MX6 |
| --- | --- | --- | --- | --- | --- | --- |
| Taste | 6.0 | 6.0 | 6.5 | 7.0 | 7.0 | 6.0 |
| Aroma | 6.0 | 6.5 | 6.5 | 7.0 | 7.5 | 7.0 |
| Overall preference (average) | 6.0 | 6.0 | 7.0 | 7.0 | 7.0 | 6.5 |

(Unit: Index)

Referring to Table 4, it can be seen that in the case of MX1, the unique taste and aroma reduced the preference using the cannabis extract alone, and in the case of using the mixture of MX2 to MX6, the preference is enhanced while the taste and aroma peculiar to the cannabis extract are neutralized by other natural extracts. In particular, in the case of using MX3 to MX5, it was confirmed that the aroma was highly evaluated and the preference was also enhanced significantly.

Therefore, in the case of using the complex extracts MX3 to MX5, it is possible to provide a functional food with higher aroma and taste in terms of preference, which has excellent effects of relieving pain and preventing or alleviating a stress-involved disease.

While preferred embodiments of the present invention have been described in detail hereinabove, it is to be understood that the scope of the present invention is not limited thereto, and various modifications and improvements made by those skilled in the art using basic concepts of the present invention, which are defined in the following claims also fall within the scope of the present invention.

What is claimed is:

1. A method of making a cannabis extract consisting essentially of:
   a) grinding cannabis to form ground cannabis;
   b) extracting the ground cannabis by using a first organic solvent to form a first extracted cannabis extract;
   c) drying the first extracted cannabis extract to form a first dried cannabis product;
   d) extracting the first dried cannabis product by using a second organic solvent to form a second extracted cannabis product;
   e) drying the second extracted cannabis product to form a second dried cannabis product; and
   f) extracting the second dried cannabis with water to form a third cannabis extract, wherein the amounts of the first organic solvent and the second organic solvent are 2 times to 50 times greater than the amount of the ground cannabis product and the first dried cannabis product; in each extracting step, each of the ground cannabis product and the first dried cannabis product are left to stand in the first organic solvent and the second organic solvent for 1 hour to 72 hours and wherein the third extract is further consisting essentially of 20 to 40 parts by weight of an *Erigeron annuus* (L.) *Pers* extract, 20 to 40 parts by weight of a *Ceratonia siliqua* (L.) *Taub.* extract, and 20 to 40 parts by weight of a *Stellaria media* extract based on 100 parts by weight of the third cannabis extract.

* * * * *